United States Patent [19]
Benvegar et al.

[11] Patent Number: 5,721,482
[45] Date of Patent: Feb. 24, 1998

[54] INTELLIGENT BATTERY AND METHOD FOR PROVIDING AN ADVANCE LOW BATTERY WARNING FOR A BATTERY POWERED DEVICE SUCH AS A DEFIBRILLATOR

[75] Inventors: Carl E. Benvegar; Gregory D. Brink, both of McMinnville, Oreg.; Dennis E. Ochs, Seattle, Wash.

[73] Assignee: Hewlett-Packard Company, Palo Alto, Calif.

[21] Appl. No.: 586,512

[22] Filed: Jan. 16, 1996

[51] Int. Cl.$^6$ .................... H01M 10/46; H01M 10/48
[52] U.S. Cl. ................................. 320/43; 320/48
[58] Field of Search ........................ 320/5, 14, 30, 320/39, 43, 44, 48; 324/426, 427, 433, 115; 340/635, 636; 429/61, 90

[56] References Cited

U.S. PATENT DOCUMENTS

| | | | |
|---|---|---|---|
| 4,703,247 | 10/1987 | Morioka | 320/40 X |
| 4,775,827 | 10/1988 | Ijntema et al. | 320/44 |
| 4,803,416 | 2/1989 | Abiven et al. | 320/44 |
| 5,099,210 | 3/1992 | Fortney et al. | 324/433 |
| 5,144,218 | 9/1992 | Bosscha | 320/44 |
| 5,155,428 | 10/1992 | Kang | 320/39 X |
| 5,250,893 | 10/1993 | Gambill et al. | 324/115 |
| 5,341,503 | 8/1994 | Gladstein et al. | 320/14 X |
| 5,345,392 | 9/1994 | Mito et al. | 324/431 X |

OTHER PUBLICATIONS

Benchmarq Microelectronics, Inc., Benchmarq 1995 Data Book, "Gas Gauge IC", pp. 2–209—2–227.

*Primary Examiner*—Edward Tso

[57] ABSTRACT

An intelligent battery having an advance low battery warning for a battery powered device is provided. The intelligent battery comprises a battery suitable for powering a battery powered device and a charge monitor circuit. The charge monitor circuit continuously measures the amount of electrical charge input and output from the battery. When the amount of charge remaining in the battery goes below a threshold amount, an advance low battery warning is generated, wherein the charge remaining in the battery is calculated by subtracting the amount of electrical charge output from the battery from the amount of electrical charge input into the battery. The low battery warning occurs independently of the output voltage of the battery such that an advance low battery warning may be provided for a battery that maintains a substantially constant output voltage until just prior to complete discharge. The circuit also includes an imminent shutdown warning circuit that measures the output voltage of the battery, and provides a battery shutdown warning when the output voltage drops below a shutdown threshold voltage. In a preferred embodiment, the battery powered device is a defibrillator/monitor, and the threshold amount is equal to a selected percent of the battery's capacity plus sufficient charge to provide a selected number of charges to a defibrillator.

21 Claims, 4 Drawing Sheets

INTELLIGENT BATTERY AND METHOD FOR PROVIDING AN ADVANCE LOW BATTERY WARNING FOR A BATTERY POWERED DEVICE SUCH AS A DEFIBRILLATOR

BACKGROUND OF THE INVENTION

1. Technical Field

The present invention relates in general to a method and system for providing an advance low battery warning, and in particular to a method and system for providing an advance low battery warning for a battery powered medical device. Still more particularly, the present invention relates to an intelligent battery for providing an advance low battery warning.

2. Description of the Related Art

In some battery powered instrument applications, it is extremely important to provide the user with an accurate, early low battery warning signal. Such a warning is particularly critical in battery powered medical devices and instruments, where a patient's life may depend on the constant availability of a charged battery. One such medical device is a defibrillator/monitor device.

Some hearts are known to periodically lapse into an irregular rhythm of rapid arrhythmias, known as fibrillation, flutter, and tachycardia. Often, these irregular rhythms require prompt management with antiarrhythmic drugs or electrical stimulation. A defibrillator applies an electric shock to a patient's heart during fibrillation, restoring the heart to a normal rhythm. Obviously, where a patient's life may depend on the constant availability of a charged battery that is powering a defibrillator/monitor device, a low battery warning signal must be provided so that the operator may replace the battery with a fully charged battery. It can be seen that designers of battery powered defibrillators and other medical instruments and devices are presented with the problem of providing a low battery warning signal that is both accurate and sufficiently advanced in time from the moment when the battery can no longer operate the instrument.

Prior solutions provide a low battery warning signal for defibrillators that is based upon the voltage across the battery terminals. Typically, a voltage threshold will be chosen as the low battery warning threshold. When the battery voltage drops below the low battery warning threshold, the low battery warning signal is turned on. The value of the low battery warning threshold is chosen at a level high enough above the instrument's minimum operating voltage so that the low battery warning signal will provide the user with a desired amount of warning time before the instrument stops working. With some battery technologies, this approach is only accurate for providing a warning which is relatively close in time to that moment when the instrument stops working. An example of such a battery technology is Nickel Cadmium that has a high charge density and has a long cycle-life, but which has a flat discharge voltage profile that remains at a nearly constant voltage for most of its discharge time and then drops off suddenly when the battery becomes depleted of charge. Prior solutions which use Nickel Cadmium battery technology require multiple battery packs in a single instrument. With such a solution, the operator would quickly switch from one battery pack to the other when one becomes depleted. Other prior solutions provide an advance low battery warning for medical instruments by using other battery technologies that have a more gradual sloping discharge voltage profile, but which are sub-optimal for some applications. For example, sealed lead acid batteries have a more gradual sloping discharge voltage profile, but are bulky, heavy, and have a substantially reduced cycle life.

What is needed is a method and system for providing an advance low battery warning for a battery powered medical device that is extremely accurate and sufficiently advanced in time from complete discharge for safe use with medical devices. This method and system would be capable of providing such a low battery warning signal for advanced, long-life batteries that have substantially flat discharge voltage profiles. Further, such a method and system would not require multiple battery packs to be included in the system, keeping the size, cost and weight at a minimum. Still further, such a method and system would provide a low battery warning earlier in time than prior solutions used with such battery technologies, and well in advance of complete discharge of the battery. This would enable the method and system to be used with medical devices such as a defibrillator to provide a low battery warning at a point where the battery still retains sufficient charge to safely power the medical device until the operator can conveniently replace the battery.

SUMMARY OF THE INVENTION

An intelligent battery, method and system for providing an advance low battery warning for a battery powered device is provided. The intelligent battery comprises a battery suitable for powering a battery powered device and a charge monitor circuit. The charge monitor circuit continuously measures the amount of electrical charge input and output from the battery. When the amount of charge remaining in the battery goes below a threshold amount, an advance low battery warning is generated, wherein the charge remaining in the battery is calculated by subtracting the amount of electrical charge output from the battery from the amount of electrical charge input into the battery. The low battery warning occurs independently of the output voltage of the battery such that an advance low battery warning may be provided for a battery that maintains a substantially constant output voltage until just prior to complete discharge. The above as well as additional objects, features, and advantages of the present invention will become apparent in the following detailed written description.

BRIEF DESCRIPTION OF THE DRAWINGS

The novel features believed characteristic of the invention are set forth in the appended claims. However, the invention, as well as a preferred mode of use, and further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
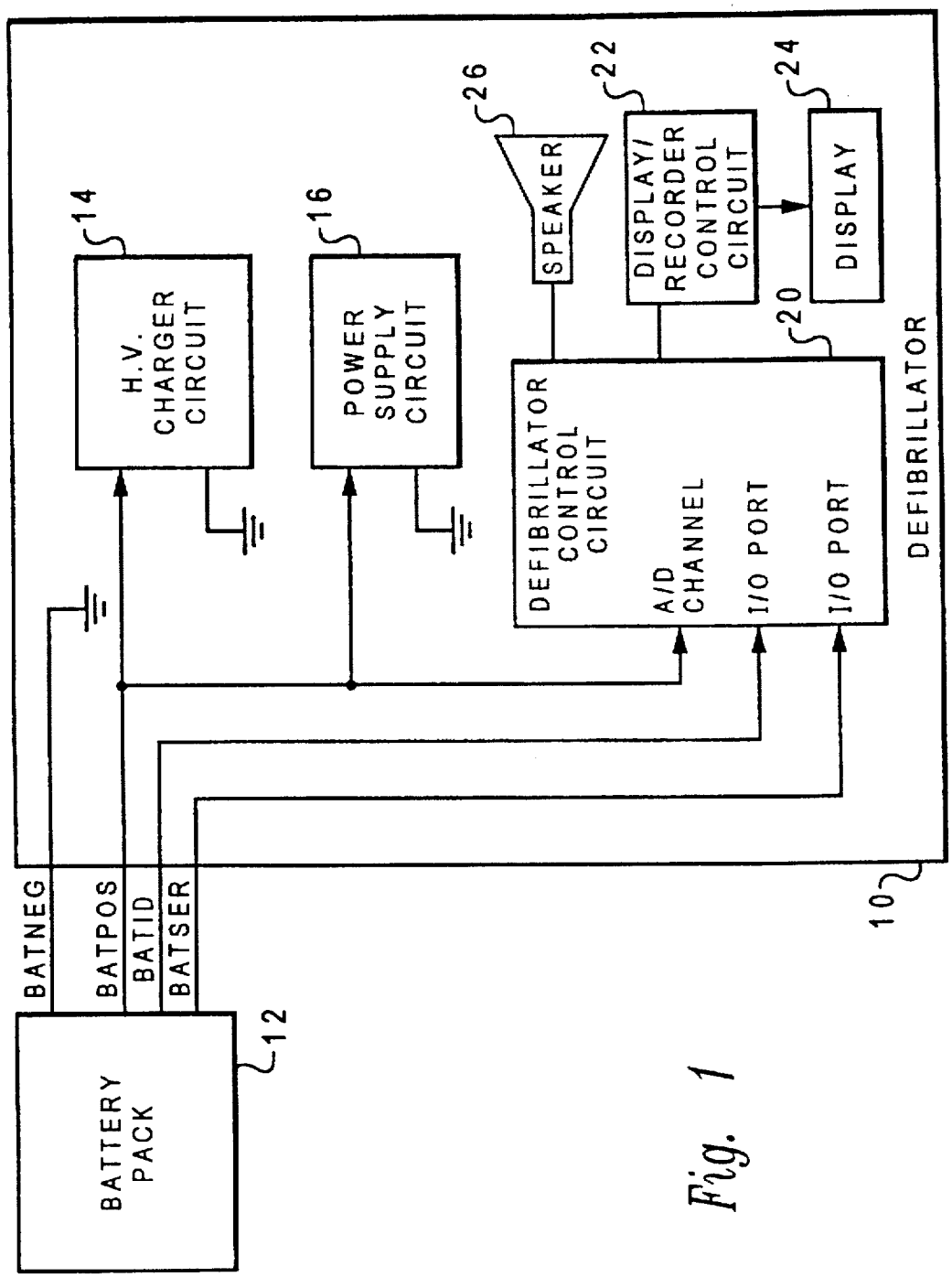
FIG. 1 shows a block diagram of a defibrillator, in accordance with a preferred embodiment of the present invention.

With reference now to the figures and in particular with reference to FIG. 1, there is shown a block diagram of a defibrillator, in accordance with the preferred embodiment of the present invention. Defibrillator 10 has a battery pack 12 attached thereto. The positive terminal (BATPOS) and the negative terminal (BATNEG) of battery pack 12 are input into defibrillator 10. Battery pack 12 also provides particular information about the condition of battery pack 12 from the serial port (BATSER). The information provided to defibrillator 10 from BATSER includes the type of battery pack attached, the total charge remaining in the battery pack 12, and a variety of calibration and self-test results. For example, battery pack 12 might be a full capacity Nickel Cadmium (NiCd) battery that provides up to 2½ hours of monitoring and up to 55 defibrillation shocks, or battery pack 12 might be a double capacity NiCd battery that provides up to 4 hours of monitoring and up to 80 defibrillation shocks. As will be appreciated by those skilled in the art, each of the connections from battery pack 12 to defibrillator 10 would be made through detachable connectors that allow easy attachment and detachment of battery pack 12 to defibrillator 10, thereby allowing simple replacement of a discharged battery pack with a charged battery pack.

As can be seen in FIG. 1, the negative terminal (BATNEG) of battery pack 12 is attached to a ground plane or bus for the circuitry of defibrillator 10. The positive terminal (BATPOS) of battery pack 12 is input into the high voltage charger circuit (H.V. Charger Circuit) 14. High voltage charger circuit 14 contains a large capacitor that is charged by battery pack 12, thereby arming the defibrillator. As will be appreciated by those skilled in the art, the large charge stored on this capacitor is used to shock the patient. The positive terminal of the battery pack 12 is also input to power supply circuit 16, which generally supplies power to the defibrillator 10, including the control and monitoring circuitry. The positive terminal of battery pack 12 is also input to the A/D Channel input of defibrillator control circuit 20. The battery serial output (BATSER) is sent to an I/O Port on defibrillator control circuit 20.

As will be explained in detail below, defibrillator control circuit 20 makes a determination of when the amount of charge remaining in the battery goes below a threshold amount; this threshold amount reflects the desired amount of charge to be remaining in a battery of the type identified by BATID for the particular application of defibrillator 10. When it is determined that the charge in the battery pack has reached this threshold amount, defibrillator control circuit 20 provides an advance low battery warning. In a preferred embodiment, defibrillator control circuit 20 provides this warning by indicating the low battery condition on display 24, such as a CRT, which is controlled by display/recorder control circuit 22. In addition, or alternatively, defibrillator control circuit 20 may produce an audio warning that is output by speaker 26. Defibrillator control circuit 20 also monitors the voltage output of battery pack 12 and when the voltage output reaches a minimum threshold limit, defibrillator control circuit 20 provides an additional audio and visual warning via speaker 26 and display 24, called a battery shutdown warning, that is distinct from the advance low battery warning and which indicates that battery shutdown is imminent.

Figure 2:
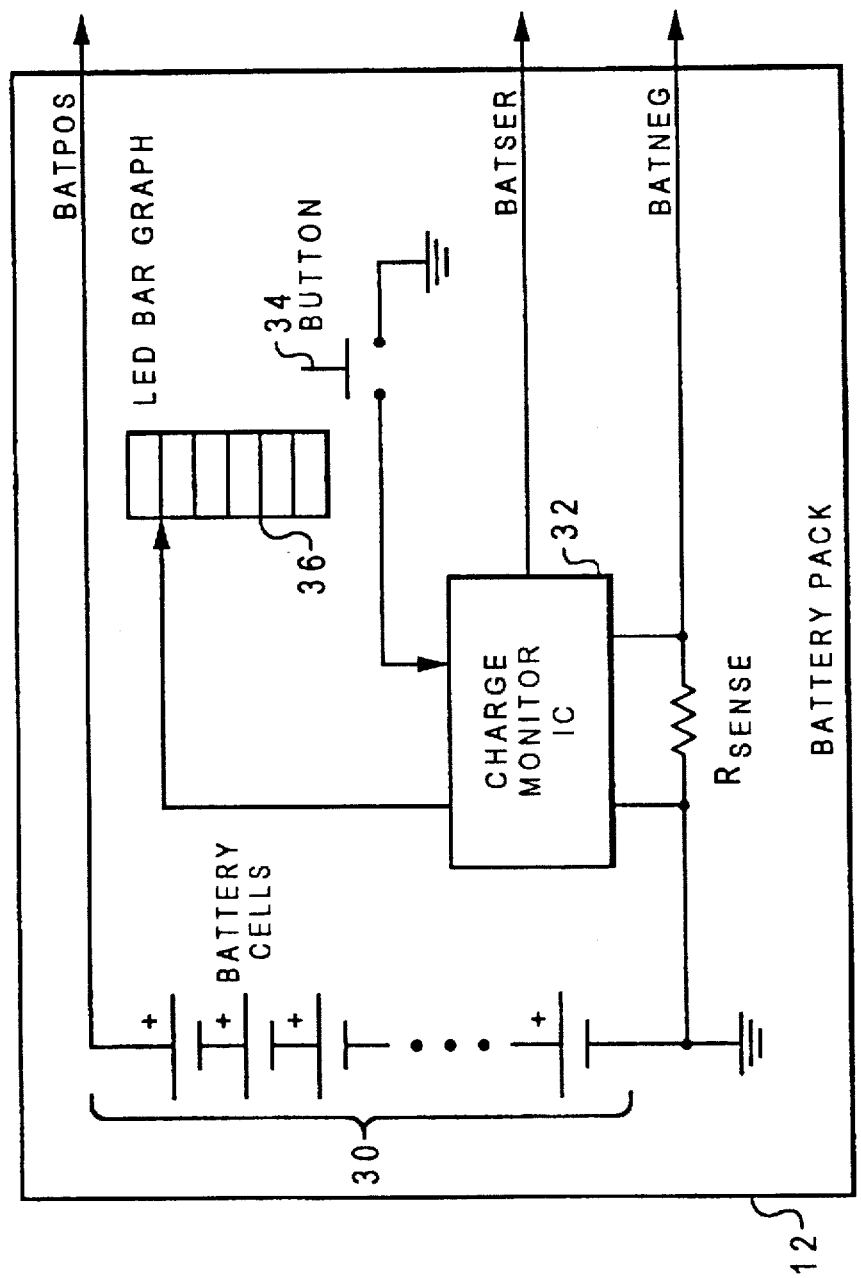
FIG. 2 shows a schematic diagram of the battery pack used in a preferred embodiment of the present invention.

Referring now to FIG. 2, there is shown a schematic diagram of the battery pack used in a preferred embodiment of the present invention. Battery pack 12 has a plurality of battery cells 30 connected in series across the positive (BATPOS) and negative (BATNEG) terminals of battery pack 12. Also contained within battery pack 12 is Charge Monitor IC 32. Charge Monitor IC 32 monitors and maintains a cumulative sum of the electrical current as it goes in and out of the battery (i.e. battery cells 30). The amount of charge input into the battery and output from the battery is continuously measured by Charge Monitor IC by measuring the voltage variations across the current sensing resister $R_{sense}$. In a preferred embodiment of the present invention, the Charge Monitor IC 32 resides on a printed circuit board mounted inside a removable Nickel Cadmium (NiCd) battery pack 12 that is used with the portable defibrillator/ monitor 10. A charge monitor IC suitable for use in the present invention as Charge Monitor IC 32 is the BQ2010 Charge Monitor IC made by Benchmarq Microelectronics of Carrolton, Tex.

Charge Monitor IC 32 reports information, including the battery state of charge in milliamp-hours (mAH), the battery's temperature in ten-degree increments of degrees celsius (C), and the Charge Monitor's status, including a plurality of calibration and testing flags, to the defibrillator/ monitor instrument 10 or a charger/maintenance system (not shown) through the serial port (BATSER). Charge Monitor IC 32 can be periodically recalibrated to the battery's exact capacity through a reconditioning cycle on a charger/ maintenance system. Such a reconditioning cycle is described in detail in co-pending application Ser. No. 08/442,435, "System Exchanging Information in a Battery Mailbox," filed on May 16 1995, on behalf of the same assignee herein. Defibrillator 10 processes the calibration and testing results communicated over BATSER to determine whether the Charge Monitor circuit is properly calibrated and whether it has a high probability of being accurate. If defibrillator 10 determines that the Charge Monitor IC 32 is not properly calibrated, it will warn the user or patient and minimize its low battery warning error (explained below).

In addition to the above features, battery pack 12 includes a button 34 and an LED Bar Graph 36. When button 34 is pressed, Charge Monitor IC 32 activates LED Bar Graph 36, which indicates the total charge remaining in battery cells 30.

Figure 3:
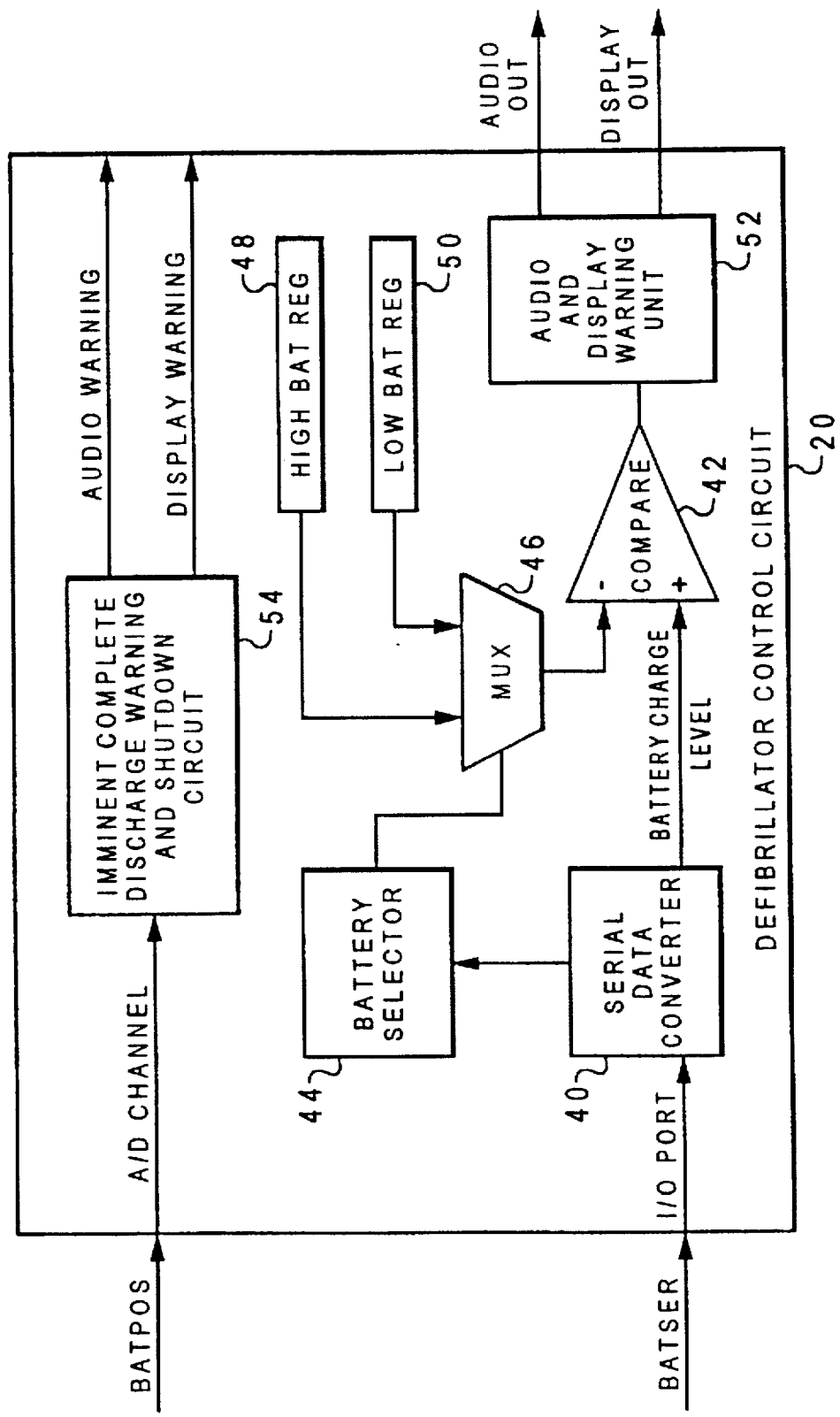
FIG. 3 shows a block diagram of the defibrillator control circuit of the present invention, as used in a preferred embodiment of the present invention.

With reference now to FIG. 3, there is shown a block diagram of the defibrillator control circuit of the present invention, in accordance with a preferred embodiment of the present invention. Defibrillator control circuit 20 receives the BATPOS and BATSER signals from battery pack 12. As has been explained, Charge Monitor IC 32 outputs serial data BATSER that includes the battery cell's 30 cumulative charge level and the type of battery pack, as well as calibration information. BATSER is received at an I/O port of serial data converter 40. Serial data converter 40 extracts all required information from the serial stream of data. The extracted battery charge level is output from serial data converter 40 and input into comparator 42 as a digital or analog value. The battery charge level indicates the amount of charge remaining in the attached battery.

Battery selector 44 receives a signal from serial data converter 40 indicating the type of battery pack attached. Based on the battery type, as indicated by this battery ID, battery selector 44 controls multiplexer (MUX) 46 to select the multiplexer output from between a high capacity battery threshold value stored in high capacity battery register (HIGH BAT REG) 48 and the low capacity battery threshold value stored in low capacity battery register (LOW BAT REG) 50. The output of multiplexer 46 is input into comparator 42 along with the battery charge level. Comparator 42 compares its inputs, which may be digital or analog values, by subtracting the negative input from the positive input. When the output of comparator 42 switches to a negative value, the negative input is greater than the positive input, and the amount of charge remaining in the battery has gone below the selected threshold amount. This event is indicated by audio and display warning unit 52 by outputting both an audio alarm to speaker 26 and a display output signal to display recorder control circuit 22. This will generate both a display and audio advance low battery warning signal on display 24 and speaker 26.

The low battery warning threshold amounts are chosen to provide sufficient advance warning to the user that the battery is getting low. This low battery warning threshold amount is based on the temperature corrected battery charge level Nominal Available Charge (NAC). In a preferred embodiment, the temperature corrected NAC (TCNAC) shall be computed as follows:

| Temperature | TCNAC |
|---|---|
| >0 C. | NAC |
| −20 C. <T <0 C. | 0.75*NAC |
| <−20 C. | 0.5*NAC |

The temperature can be determined by reading a temperature measuring register on Charge Monitor IC 32.

In a preferred embodiment of the present invention, it has been determined that an advance low battery warning for the defibrillator of the present invention is desired at the point when the battery pack has enough charge remaining to operate the defibrillator for thirty minutes of monitoring and to perform five 360 joule (J) charges. Therefore, the amount of TCNAC required for this performance is computed as follows:

| Monitoring: | 0.8 Amps * 0.5 hours = | 400 mAH |
|---|---|---|
| 5 360J Charges: | 5 * 15 Amps * 3.5 Seconds/3600 Seconds = | 73 mAH |
| Total: | 400 mAH + 73 mAH = | 473 mAH |

As used in a preferred embodiment of the present invention, battery pack 12 is a NiCd battery. As will be appreciated, a medical instrument such as a defibrillator should only be shut off when it can no longer function as a monitor and perform high voltage charges. It has been shown that this voltage threshold is 11.4 Volts. With the battery monitoring voltage at 11.4 V, the charge time is typically greater than 10 seconds, and when the instrument shuts down, there is typically less than 10% of the charge remaining in the battery. Therefore, the amount of charge remaining in the battery when the output voltage reaches this threshold value is calculated as 10% of the total capacity for the battery. This is computed for two types of batteries as follows:

| High Capacity battery | 0.10 * 4000 mAH = 400 mAH |
|---|---|
| Low Capacity battery | 0.10 * 2500 mAH = 250 mAH |

Finally, the low battery threshold amount of charge for these two types of batteries, wherein the high capacity battery is a 4000 milliamp-hour (mAH) and the low capacity battery is a 2500 milliamp-hour (mAH), is calculated as follows for the given performance requirements:

| High Capacity battery | 473 mAH + 400 mAH = 873 mAH |
|---|---|
| Low Capacity battery | 473 mAH + 250 mAH = 723 mAH |

Figure 4:
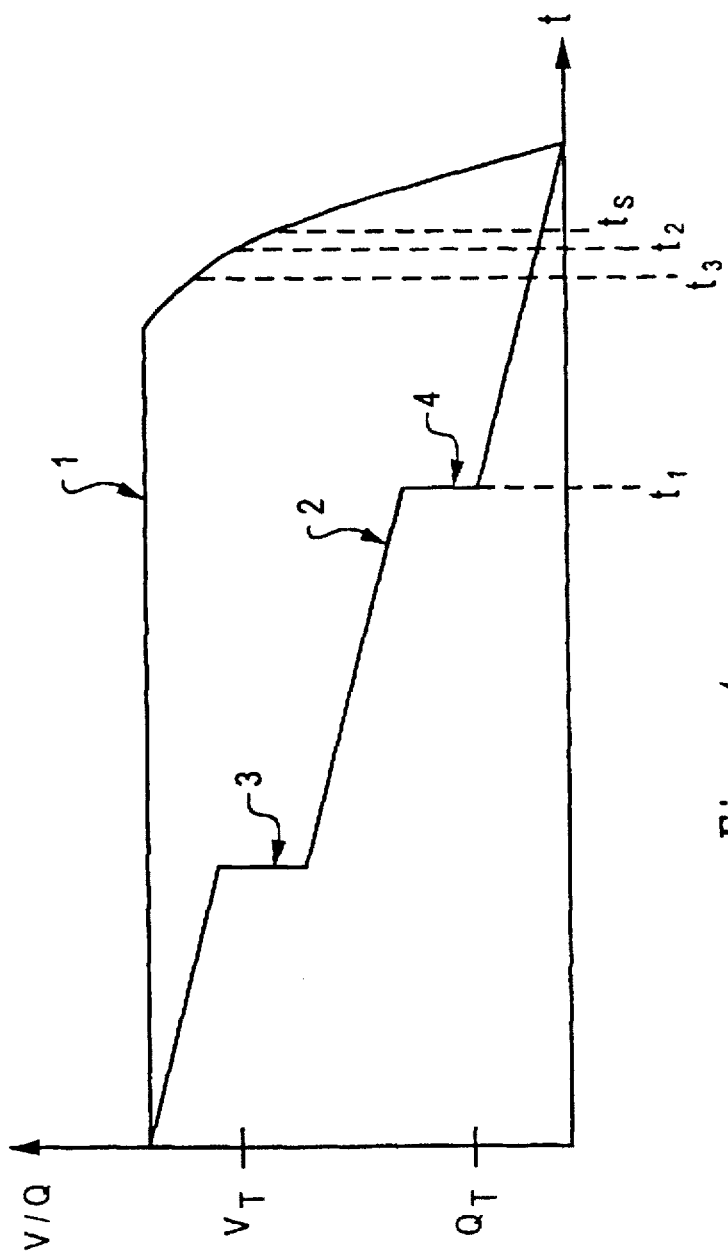
FIG. 4 is a sample graph of the voltage curve and charge curve of the battery pack powering the battery powered defibrillator in a preferred embodiment of the present invention.

Referring back to FIG. 3, the high capacity, low battery threshold amount would be loaded into the high capacity battery register 48 and the low capacity, low battery threshold amount would be loaded into the low capacity battery register 50. FIG. 4 is one example of a graph of the voltage curve 1 and charge curve 2 over time for battery pack 12, while powering the battery powered defibrillator 10. The vertical axis shows voltage (V) and charge (Q) and the horizontal axis shows time (t). The low battery threshold amount is indicated as $Q_T$. As seen from the graph, the charge curve 2 shows a steadily declining discharge of battery pack 12 as it supplies power supply circuit 16 to provide the monitoring features of defibrillator 10. At points 3 and 4 in charge curve 2, there has occurred a rapid discharge of battery pack 12 to charge high voltage charger circuit 14 after defibrillator 10 has provided two shocks to the patient. In this example, the second discharge 4 has brought the charge remaining in the battery (Q) to below the charge threshold amount ($Q_T$).

If battery pack 12 is identified as a high capacity battery, the battery charge level input to the positive input of comparator 42 has dropped below 873 mAH input at the negative input of comparator 42 from high capacity battery register 48 through multiplexer 46. If battery pack 12 is a low capacity battery, then the battery charge level at the positive input of comparator 42 has dropped below 723 mAH indicated by the input to the negative terminal of comparator 42 from low capacity battery register 50 through multiplexer 46. Therefore, the defibrillator control circuit 20 will generate an audio and display advance low battery warning at time $t_1$.

Referring back to FIG. 3, defibrillator control circuit 20 receives BATPOS at the A/D channel of Imminent Complete Discharge Warning and Shutdown Circuit (ICDWSC) 54. ICDWSC 54 converts the output voltage of battery pack 12 to a digital value, and in a manner known to those skilled in the art and as used in prior solutions, ICDWSC 54 senses when the battery pack output voltage drops below a threshold voltage ($V_T$). When this occurs, ICDWSC 54 produces an audio and display warning on display 24 and speaker 26 that indicates to the user that a shutdown of defibrillator 10 is imminent and that battery pack 12 should be immediately replaced. As seen in FIG. 4, ICDWSC 54 detects when voltage curve 1 drops below the threshold voltage ($V_T$), at which time, it produces an audio and display battery shutdown warning, as shown at time $t_2$. Sometime shortly thereafter, at time $t_5$, ICDWSC 54 will shutdown defibrillator 10.

In the event that serial data converter 40 detects a calibration flag in the serial data BATSER indicating that Charge Monitor IC 32 is not functioning or that battery pack 12 does not have valid calibration, then the low battery shutdown warning output by audio and display warning unit 52 is disabled. The operation of the calibration flag is described in detail in application Ser. No. 08/442,435, "System Exchanging Information in a Battery Mailbox," filed on May 16 1995, on behalf of the same assignee herein. In that situation, ICDWSC 54 acts as a backup warning system by producing the low battery warning in the manner seen in the prior art. The low battery warning will be produced by ICDWSC 54 at a time $t_3$ when voltage curve 1 drops below a preselected low battery voltage threshold that is greater than the battery shutdown warning threshold ($V_T$). Although not an advance warning, as would be provided by audio and display warning unit 52, this low battery warning can act as a backup warning system when the Charge Monitor IC 32 is not functioning or battery pack 12 is not calibrated.

Finally, reference to the graph of FIG. 4 illustrates the significant advantages of the present invention. As shown by charge curve 2, the method and system of the present invention will provide an advance low battery warning at time $t_1$, well in advance of the time the battery completely discharges and the defibrillator control circuit shuts the defibrillator down. Moreover, the charge threshold amount that triggers the advance low battery shutdown warning can be customized to the type and capacity of battery pack attached to the defibrillator and to a level that provides the necessary amount of charge to operate the battery powered device for as long as it is needed to safely power the defibrillator before the battery pack is replaced. This capability of customizing the amount of charge in reserve after the advance low battery warning occurs is particularly advantageous for battery powered medical instruments and devices such a defibrillator/monitor where a patient's life may depend on the constant availability of a charged battery. Therefore, this invention provides a means for a low battery warning signal that is both accurate and also sufficiently advanced in time from the moment when the battery can no longer operate the instrument.

This advantage of the present invention is exemplified in FIG. 4 by the difference in time from time $t_1$ to the shutdown time $t_5$ and the time from $t_2$ to the shutdown time $t_5$. Prior solutions had provided a low battery shutdown warning based on a threshold decrease of the voltage output of the battery pack. Therefore, the low battery shutdown warning would be generated in a manner similar to the low battery warning produced by ICDWSC 54. With the prior solutions, a medical instrument powered by the superior battery technologies, such as Nickel Cadmium, would have a very flat discharge voltage profile, and would be incapable of providing a low battery warning well in advance of the battery shutdown time ($t_5$). Instead, the earliest time the low battery warning may occur is after the voltage begins to decline, for example at time $t_2$, as indicated by voltage curve 1. The present invention, on the other hand, can provide a very accurate low battery warning at any selected time (mAH) in advance of the medical instrument shutdown. In summary, the present invention provides a low battery warning signal that is more accurate and more advanced in time from the point when the instrument will no longer operate than any method, system or device in the prior art.

In an alternative embodiment of the present invention, the defibrillator control circuit is contained within and formed as an integral part of the battery pack. This embodiment provides an intelligent battery that produces an advance low battery warning for a battery powered defibrillator. Moreover, while the invention has been particularly shown and described with reference to preferred embodiments of a method and system for providing an advance low battery warning for a battery powered defibrillator, it will be appreciated that the present invention can be utilized with any battery powered medical device, or generally with any battery powered device, and that the scope of the present invention is intended to encompass such alternative embodiments. While the invention has been particularly shown and described with reference to a preferred embodiment, it will be understood by those skilled in the art that various changes in form and detail may be made therein without departing from the spirit and scope of the invention.

What is claimed is:

1. A method for providing an advance low battery warning for a battery powered device, the method comprising the steps of:
   measuring the amount of electrical charge input into a battery;
   measuring the amount of electrical charge output from the battery; and
   generating an advance low battery warning that indicates when the amount of charge remaining in the battery goes below a threshold amount, wherein the charge remaining in the battery is calculated by subtracting the amount of electrical charge output from the battery from the amount of electrical charge input into the battery;
   wherein the advance low battery warning is generated independently of an output voltage from the battery such that the method can provide an advance low battery warning for a battery that maintains a substantially constant output voltage until just prior to complete discharge.

2. A method for providing an advance low battery warning for a battery powered device according to claim 1, wherein the battery powered device is a medical instrument, and wherein the step of indicating occurs when a charge level for the battery for the medical instrument reaches the threshold amount.

3. A method for providing an advance low battery warning for a battery powered device according to claim 2, wherein the medical instrument is a battery powered defibrillator/monitor.

4. A method for providing an advance low battery warning for a battery powered device according to claim 3, wherein the threshold amount is equal to a selected percentage of the battery's capacity plus sufficient charge to provide a selected number of charges to a defibrillator.

5. A method for providing an advance low battery warning for a battery powered device according to claim 1, further comprising the steps of checking the calibration of the battery powered device and utilizing a backup warning method to provide the low battery warning if the calibration is invalid.

6. A method for providing an advance low battery warning for a battery powered device according to claim 5, wherein the backup warning method comprises the steps of measuring the output voltage of the battery, and providing a low battery warning when the output voltage drops below a low battery threshold voltage.

7. A method for providing an advance low battery warning for a battery powered device according to claim 1, further comprising the steps of measuring the output voltage of the battery, and providing a battery shutdown warning when the output voltage drops below a shutdown threshold voltage.

8. A system for providing an advance low battery warning for a battery powered device, comprising:
   means for measuring the amount of electrical charge input into a battery;
   means for measuring the amount of electrical charge output from the battery; and
   means for generating an advance low battery warning that indicates when the amount of charge remaining in the battery goes below a threshold amount, wherein the charge remaining in the battery is calculated by subtracting the amount of electrical charge output from the battery from the amount of electrical charge input into the battery;

wherein the advance low battery warning is generated independently of an output voltage from the battery such that the system can provide an advance low battery warning for a battery that maintains a substantially constant output voltage until just prior to complete discharge.

9. A system for providing an advance low battery warning for a battery powered device according to claim 8, wherein the battery powered device is a medical instrument, and wherein the step of indicating occurs when a charge level for the battery for the medical instrument reaches the threshold amount.

10. A system for providing an advance low battery warning for a battery powered device according to claim 9, wherein the medical instrument is a battery powered defibrillator/monitor.

11. A system for providing an advance low battery warning for a battery powered device according to claim 10, wherein the threshold amount is equal to a selected percent of the battery's capacity plus sufficient charge to provide a selected number of charges to a defibrillator.

12. A system for providing an advance low battery warning for a battery powered device according to claim 8, further comprising means for checking the calibration of the battery powered device and utilizing a backup warning system to provide the low battery warning if the calibration is invalid.

13. A system for providing an advance low battery warning for a battery powered device according to claim 12, wherein the backup warning system comprising means for measuring the output voltage of the battery, and providing a low battery warning when the output voltage drops below a low battery threshold voltage.

14. A system for providing an advance low battery warning for a battery powered device according to claim 8, further comprising means for measuring the output voltage of the battery, and providing a battery shutdown warning when the output voltage drops below a shutdown threshold voltage.

15. An intelligent battery having an advance low battery warning for a battery powered device, comprising:

a battery suitable for powering a battery powered device; and a charge monitor circuit that measures the amount of electrical charge input into the battery and measures the amount of electrical charge output from the battery, and further generates an advance low battery warning that indicates when the amount of charge remaining in the battery goes below a threshold amount, wherein the charge remaining in the battery is calculated by subtracting the amount of electrical charge output from the battery from the amount of electrical charge input into the battery;

wherein the advance low battery warning is generated independently of an output voltage from the battery such that an advance low battery warning may be provided for a battery that maintains a substantially constant output voltage until just prior to complete discharge.

16. An intelligent battery according to claim 15, wherein the battery powered device is a medical instrument, and wherein the step of indicating occurs when a charge level for the battery for the medical instrument reaches the threshold amount.

17. An intelligent battery according to claim 16, wherein the medical instrument is a battery powered defibrillator/monitor.

18. An intelligent battery according to claim 17, wherein the threshold amount is equal to a selected percent of the battery's capacity plus sufficient charge to provide a selected number of charges to a defibrillator.

19. An intelligent battery according to claim 15, wherein the charge monitor circuit checks the calibration of the battery powered device and further comprising a backup warning device that is utilized as a backup warning device to provide the low battery warning if the calibration is invalid.

20. An intelligent battery according to claim 19, wherein the backup warning device comprises means for measuring the output voltage of the battery, and providing a low battery warning when the output voltage drops below a low battery threshold voltage.

21. An intelligent battery according to claim 15, further comprising means for measuring the output voltage of the battery, and providing a battery shutdown warning when the output voltage drops below a shutdown threshold voltage.

* * * * *